United States Patent [19]

Yamamoto et al.

[11] Patent Number: 4,596,796
[45] Date of Patent: Jun. 24, 1986

[54] DITHIOLPHOSPHORIC ACID ESTER AS A SOIL PESTICIDE

[75] Inventors: Haruyasu Yamamoto, Takarazuka; Kiyoshi Kasamatsu, Kobe; Takayuki Okabe, Nishinomiya, all of Japan

[73] Assignee: Sumitomo Chemical Company, Limited, Osaka, Japan

[21] Appl. No.: 648,986

[22] Filed: Sep. 10, 1984

[30] Foreign Application Priority Data

Sep. 12, 1983 [JP] Japan ................................. 58-168877
Sep. 13, 1983 [JP] Japan ................................. 58-170346

[51] Int. Cl.$^4$ ....................... A01N 57/12; C07F 9/165
[52] U.S. Cl. .................................. 514/143; 558/100; 558/123
[58] Field of Search ......................... 260/963; 514/143

[56] References Cited

U.S. PATENT DOCUMENTS

| 3,112,244 | 11/1963 | Goyette | 260/963 |
| 3,268,393 | 8/1966 | Wilson | 514/143 |
| 3,689,603 | 9/1972 | Nishino et al. | 260/963 |
| 3,725,546 | 4/1973 | Tsuchiya et al. | 260/963 |
| 3,760,042 | 9/1973 | Beriger et al. | 260/963 |
| 4,273,769 | 6/1981 | Koyanagi et al. | 260/963 |
| 4,383,991 | 5/1983 | Gough | 260/963 |

FOREIGN PATENT DOCUMENTS 0107957  5/1984  European Pat. Off. .
WO83/00870  3/1983  World Int. Prop. O. .

Primary Examiner—Anton H. Sutto
Attorney, Agent, or Firm—Stevens, Davis, Miller & Mosher

[57] ABSTRACT

A dithiolphosphoric acid ester of the formula,

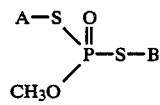

wherein A is sec-butyl or tert-butyl group, and B is iso-propyl, n-butyl, iso-butyl, sec-butyl or tert-butyl group, which is useful as a soil pesticidal composition for pests in soil.

4 Claims, No Drawings

DITHIOLPHOSPHORIC ACID ESTER AS A SOIL PESTICIDE

The present invention relates to a dithiolphosphoric acid ester of the formula (I) (hereinafter referred to as present compound),

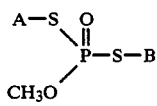 (I)

wherein A is sec-butyl or tert-butyl group, and B is iso-propyl, n-butyl, iso-butyl, sec-butyl or tert-butyl group, its production and soil pesticidal compositions containing it as an active ingredient.

That some kinds of dithiolphosphoric acid ester, for example, O-ethyl, S,S-di-n-butyl dithiolphosphate, etc., can be used as an active ingredient for insecticides, acaricides and nematocides, is described in Japanese Patent Publication No. 29847/1969; and also that, for example, O-ethyl S-sec-butyl S-tert-butyl dithiolphosphate, etc., can be used as an active ingredient for nematocides and soil pesticides, is described in International Patent Publication No. WO 83/00870. But, it may not always be said that these compounds are always satisfactory as an active ingredient for soil pesticides.

While, the present compound, as compared with these compounds, has a high controlling activity against pests living in soil and doing damage to paddy rice, vegetables, flowers, lawn grasses, fruit trees, tea, mulberry and the like, and besides said compound gives no such phytotoxicity as to become a problem to these plants.

The present compound, therefore, can be used as an active ingredient for soil pesticidal compositions used for paddy fields, plowlands, orchards, pastures, tea gardens, mulberry farms and the like.

The soil pest includes for example pests of Diabrotica genus such as western corn rootworm (*Diabrotica virgifera* Le Conte), northern corn rootworm (*Diabrotica longicornis* Say), southern corn rootworm (*Diabrotica undecimpunctata howardi* Barber), etc., pests of Anomala genus such as cupreous chafer (*Anomala cuprea* Hope), soybean beetle (*Anomala rufocuprea* Motschulsky), cherry chafer (*Anomala daimiana,* Harlod), striated chafer (*Anomala testaceips* Motschulsky), etc., pests of Popillia genus such as Japanese beetle (*Popillia japonica* Newman), etc., pests of Aulacophora genus such as cucurbit leaf beetle (*Aulacophora femoralis* Motschulsky), etc., pests of Phyllotreta genus such as striped cabbage flea beetle (*Phyllotreta vittata* Fabricius), etc., pests of Melanotus genus such as sweetpotato wireworm (*Melanotus caudex* Lewis), etc., pests of Agriotes genus such as barley wireworm (*Agriotes fuscicollis* Miwa), etc., pests of Hylemya genus such as onion maggot (*Hylemya antiqua* Meigen), turnip maggot (*Hylemya floralis* Fallén), seed-corn maggot (*Hylemya platura* Meigen), etc., pests of Agrotis genus such as common cutworm (*Agrotis segetum* Denis et Schiffermüller), black cutworm (*Agrotis ipsilon* Hufnagel), etc., pests of Grylloptalpa genus such as African mole cricket (*Gryllotalpa africana* Palisot de Beauvois), etc., pests of Lissorhoptrus genus such as ricewater weevil (*Lissorhoptrus oryzophilus* Kuschel), etc., pests of Pratylenchus genus such as Cobb root-lesion nematode (*Pratylenchus penetrans* Cobb), walnut root-lesion nematode (*Pratylenchus vulnus* Allen et Jensen), coffee root-lesion nematode (*Pratylenchus coffeae* Zimmermann), etc., pests of Heterodera genus such as soybean cyst nematode (*Heterodera glycines* Ichinohe), etc., pests of Meloidogyne genus such as northern root-knot nematode (*Meloidogyne hapla* Chitwood), cotton root-knot nematode (*Meloidogyne incognita* var. acrita Chitwood), Javanese root-knot nematode (*Meloidogyne javanica* Treub), peanut root-knot nematode (*Meloidogyne arenaria* Neal), etc., pests of Aphelenchoides genus such as rice white-tip nematode (*Aphelenchoides besseyi* Christie) and the like.

The present compound can be produced by reacting a halogenated thiophosphoric acid derivative of the formula (II),

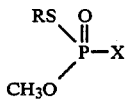 (II)

wherein R is iso-propyl, n-butyl, iso-butyl, sec-butyl or tert-butyl group and X is halogen atom, with an alkylmercaptan of the formula (III), $$R'SH \qquad (III)$$

wherein R' is B when R is A and is A when R is B (in which A and B are each as defined above).

The reaction is carried out in a solvent or without a solvent, preferably in the presence of a dehydrohalogenating agent and a phase transfer catalyst or copper catalyst.

As to the amount of the alkylmercaptan (III) and dehydrohalogenating agent which are a reagent used for reaction, the amount of the alkylmercaptan (III) is 1 to 5 equivalents based on 1 equivalent of the halogenated thiophosphoric acid derivative (II), and that of the latter is 1 to 1.5 equivalents based on 1 equivalent of the same.

The reaction temperature is about −10° C. to about 50° C., and the reaction time is about 30 minutes to about 5 hours.

The solvent includes for example ketones (e.g. acetone, methyl ethyl ketone, methyl isobutyl ketone, cyclohexanone), halogenated hydrocarbons (e.g. chloroform, carbon tetrachloride, dichloroethane, chlorobenzene, dichlorobenzene), aromatic hydrocarbons (e.g. benzene, toluene, xylene), aliphatic hydrocarbons (e.g. n-hexane, n-heptane, cyclohexane), nitriles (e.g. acetonitrile, isobutyronitrile), water and mixtures thereof.

The dehydrohalogenating agent includes for example organic bases such as pyridine, triethylamine, N,N-diethylaniline, etc., and inorganic bases such as sodium hydroxide, potassium hydroxide, sodium carbonate, potassium carbonate, etc. The phase transfer catalyst includes for example tetraalkylammonium halides such as tetrabutylammonium bromide, triethylbenzylammonium chloride, etc., and the copper catalyst includes for example copper powder, cuprous chloride, etc.

After completion of the reaction, after-treatment is carried out as usual, and if necessary, the product obtained is purified by chromatography, distillation and the like.

Also, the present compound can be produced by reacting a dithiophosphoric acid salt of the formula (IV),

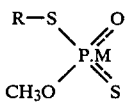

wherein R is iso-propyl, n-butyl, iso-butyl, sec-butyl or tert-butyl group, and M is alkali metal atom, with a halogenated alkyl of the formula (V), $$R'-Y \quad (V)$$

wherein R' is B when R is A and is A when R is B (in which A and B are each as defined above), and Y is halogen atom.

The reaction is carried out in a solvent or without a solvent.

The amount of the halogenated alkyl (V) which is a reagent used for reaction, is 1 to 10 equivalents based on 1 equivalent of the dithiophosphoric acid salt (IV).

The reaction temperature is about 20° C. to about 80° C., and the reaction time is about 30 minutes to about 3 hours.

The solvent includes, in addition to the foregoing ketones, halogenated hydrocarbons, aromatic hydrocarbons, aliphatic hydrocarbons, nitriles, water, etc., alcohols (e.g. methanol, ethanol, isopropanol, tert-butanol, methyl cellosolve) and mixtures thereof.

After completion of the reaction, after-treatment is carried out in the same manner as above, and the product obtained is purified if necessary.

Further, the present compound can also be produced by reacting O-methyl S,S-dialkyl phosphite of the formula (VI),

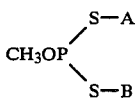

wherein A and B are each as defined above, with an oxidizing agent.

The reaction is generally carried out in a solvent.

The amount of the oxidizing agent (e.g. hydrogen peroxide) which is a reagent used for reaction, is 1 to 3 equivalents based on 1 equivalent of O-methyl S,S-dialkyl phosphite (VI).

The reaction temperature is about 0° C. to about 70° C., and the reaction time is about 30 minutes to about 3 hours.

The solvent includes the foregoing ketones, halogenated hydrocarbons, aromatic hydrocarbons and aliphatic hydrocarbons, water and mixtures thereof. After completion of the reaction, after-treatment is carried out in the same manner as described above, and the product obtained is purified if necessary.

O-methyl S,S-dialkyl phosphite of the formula (VI), which is a starting compound, can be produced by reacting S,S-dialkyl chlorophosphite of the formula (VII),

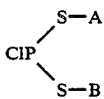

wherein A and B are each as defined above, with methanol in the presence of a dehydrochlorinating agent, and said S,S-dialkyl chlorophosphite can be produced, for example, by reacting phosphorus trichloride with an alkylmercaptan in a solvent not disturbing this reaction in the presence of a dehydrochlorinating agent.

The solvent includes the foregoing halogenated hydrocarbons, aromatic hydrocarbons and aliphatic hydrocarbons, and the like. The dehydrochlorinating agent includes organic bases such as triethylamine, pyridine, N,N-dimethylaniline and the like.

Production examples for the present compound will be shown.

PRODUCTION EXAMPLE 1 [Production of the present compound (4)]

3.0 Grams of potassium O-methyl S-sec-butyl phosphorodithioate was dissolved in 50 ml of acetone, and after adding 3.5 g of n-butyl bromide, the mixture was refluxed for 3 hours with stirring. After completion of the addition, acetone was removed under reduced pressure, and toluene was added to the residue. The mixture was washed with 3% aqueous sodium hydrogencarbonate and then with water, and toluene was removed under reduced pressure to obtain 2.5 g of a pale yellow and oily product as a residue. This product was purified by column chromatography on silica gel to obtain 1.8 g of a colorless and oily O-methyl S-sec-butyl S-n-butyl phosphorodithiolate.

$n_D^{23}$: 1.5022.

PRODUCTION EXAMPLE 2 [Production of the present compound (1)]

To a solution of 9.0 g of O-methyl S-sec-butyl phosphorochloridothioate in 15 ml of toluene were added 4.0 g of iso-butylmercaptan and a catalytic amount of tetrabutylammonium bromide. Thereafter, 3.6 g of 50% aqueous sodium hydroxide solution was added dropwise over 1 hour with stirring while cooling the reaction mixture so that the inner temperature was 0° to 10° C., and then stirring was continued at room temperature for further 1 hour. After completion of the reaction, the reaction mixture was washed with 3% aqueous sodium hydroxide and then with water, and toluene was removed under reduced pressure. The oily product obtained as a residue was purified by column chromatography on silica gel to obtain 6.3 g of a pale yellow and oily O-methyl S-sec-butyl S-iso-butyl phosphorodithiolate.

$n_D^{21}$: 1.5015.

PRODUCTION EXAMPLE 3 [Production of the present compound (7)]

To a solution of 7.0 g of O-methyl S,S-di-tert-butyl phosphite in 70 ml of n-hexane was added dropwise 6.5 g of 30% aqueous hydrogen peroxide at 25° C., and after stirring at 50° C. for 1 hour, the mixture was cooled to room temperaure. The hexane layer was washed with water, dried over anhydrous sodium sulfate and concentrated under reduced pressure to obtain 10 g of a pale brown and oily product as a residue. This product was purified by column chromatography on silica gel to obtain 6.3 g of a colorless and oily O-methyl S,S-di-tert-butyl phosphorodithiolate.

$n_D^{21}$: 1.5045.

Examples of the present compound which can be produced by these method are shown in Table 1.

TABLE 1

Dithiolphosphoric acid esters of the formula,

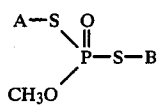

| Compound No. | A | B | Physical constant |
|---|---|---|---|
| (1) | sec-C$_4$H$_9$ | iso-C$_4$H$_9$ | n$_D^{21}$ 1.5015 |
| (2) | tert-C$_4$H$_9$ | iso-C$_4$H$_9$ | n$_D^{21}$ 1.5018 |
| (3) | sec-C$_4$H$_9$ | iso-C$_3$H$_7$ | n$_D^{22}$ 1.5035 |
| (4) | sec-C$_4$H$_9$ | n-C$_4$H$_9$ | n$_D^{23}$ 1.5022 |
| (5) | sec-C$_4$H$_9$ | sec-C$_4$H$_9$ | n$_D^{22}$ 1.5022 |
| (6) | sec-C$_4$H$_9$ | tert-C$_4$H$_9$ | n$_D^{21}$ 1.5035 |
| (7) | tert-C$_4$H$_9$ | iso-C$_3$H$_7$ | n$_D^{21}$ 1.5060 |
| (8) | tert-C$_4$H$_9$ | n-C$_4$H$_9$ | n$_D^{21}$ 1.5040 |
| (9) | tert-C$_4$H$_9$ | tert-C$_4$H$_9$ | n$_D^{21}$ 1.5045 |

When the present compounds are used as an active ingredient for soil pesticidal compositions, they are generally formulated into oil sprays, emulsifiable concentrates, wettable powders, granules, dusts, aerosols, etc. by mixing with a solid, liquid or gaseous carrier and if necessary, adding auxiliaries for formulation such as surface active agents and others.

These compositions contain 0.1 to 99.9% by weight, preferably 1 to 80% by weight of the present compound as an active ingredient.

The solid carrier includes for example fine powders or granules of clays (e.g. kaolin clay, attapulgite clay, diatomaceous earth, synthetic hydrated silicon dioxide, Fubasami clay, bentonite, terra abla), talcs, other inorganic minerals (e.g. sericite, quartz powder, sulfur powder, activated carbon, calcium carbonate, hydrated silica), chemical fertilizers (e.g. ammonium sulfate, ammonium phosphate, ammonium nitrate, urea, ammonium chloride) and the like. The liquid carrier includes for example water, alcohols (e.g. methanol, ethanol), ketones (e.g. acetone, methyl ethyl ketone), aromatic hydrocarbons (e.g. benzene, toluene, xylene, ethylbenzene, methylnaphthalene), aliphatic hydrocarbons (e.g. n-hexane, cyclohexanone, kerosene), esters (e.g. ethyl acetate, butyl acetate), nitriles (e.g. acetonitrile, isobutyronitrile), ethers (e.g. dioxane, diisopropyl ether), acid amides (e.g. dimethylformamide, dimethylacetamide), halogenated hydrocarbons (e.g. dichloroethane, trichloroethylene, carbon tetrachloride) and the like. The gaseous carrier, i.e. propellant, includes for example freon gas, butane gas, carbon dioxide gas and the like.

The surface active agent includes for example alkyl sulfates, alkylsulfonates, alkylarylsulfonates, alkyl aryl ethers and their polyoxyethylenized products, polyethylene glycol ethers, polyhydric alcohol esters, sugar alcohol derivatives and the like.

The fixing agent and dispersing agent include for example casein, gelatin, polysaccharides (e.g. starch powder, gum arabic, cellulose derivatives, alginic acid), lignin derivatives, bentonite, saccharides, synthetic water-soluble high polymers (e.g. polyvinyl alcohol, polyvinyl pyrrolidone, polyacrylic acids) and the like. The stabilizer includes for example PAP (isopropyl acid phosphate), BHT (2,6-di-tert-butyl-4-methylphenol), BHA (mixture of 2-tert-butyl-4-methoxyphenol and 3-tert-butyl-4-methoxyphenol), vegetable oils, mineral oils, the foregoing surface active agents, fatty acids and their esters and the like.

Formulation examples for the present compound will be shown.

The present compound is shown by Compound No. in Table 1. Parts in the examples are by weight.

FORMULATION EXAMPLE 1: Emulsifiable concentrate

To 40 parts of each of the present compounds (1) to (9) are added 50 parts of xylene and 10 parts of Sorpol SM-200, an emulsifier (mixture of polyoxyethylene alkylaryl ether, etc. and dodecylbenzenesulfonic acid), and the mixture is well mixed by stirring to obtain a 40% emulsifiable concentrate of each compound.

FORMULATION EXAMPLE 2: Wettable powder

To 40 parts of each of the present compounds (1) to (9) is added 7.5 parts of Sorpol SM-200, an emulsifier, and the mixture is well mixed. Thereafter, 20 parts of Carplex #80 (synthetic hydrated silicon dioxide fine powder) and 35 parts of 300-mesh diatomaceous earth are added, and the mixture is well mixed by stirring on a juice mixer to obtain a 40% wettable powder of each compound.

FORMULATION EXAMPLE 3: Granule

15 Parts of each of the present compounds (1) to (9) is mixed with and dissolved in 10 parts of diethylene glycol. The resulting solution is well mixed with 75 parts of Attapulgus clay 25/50 mesh (attapulgite clay produced by Engelhard Co.) on the Nauta mixer while spraying the solution onto the clay. A 15% granule of each compound is thus obtained.

FORMULATION EXAMPLE 4: Dust

To 5 parts of each of the present compound (1) to (9) are added 20 parts of acetone, 3 parts of Carplex #80, 0.3 part of PAP and 91.7 parts of 300-mesh talc. The mixture is well mixed by stirring on a juice mixer and acetone is removed by evaporation to obtain a 5% dust of each compound.

FORMULATION EXAMPLE 5: Oil spray

To 20 parts of each of the present compounds (1) to (9) is added 80 parts of kerosene, and the mixture is well mixed to obtain a 20% oil spray of each compound.

These compositions may be used, as such or as aqueous dilute liquors, by spraying or scattering onto soil surface and if necessary, mixing with the soil after spraying or scattering, or drenching soil. Sometimes, they may be used in foliar spraying. Also, they may be used in mixtures with other insecticides, acaricides, nematocides, fungicides, seed disinfectants, fertilizers or soil improvers, or may be used at the same time together with these chemicals without mixing.

When the present compound is used as an active ingredient for soil pesticidal compositions, its dosage rate is generally 10 to 1000 g/10 ares, preferably 50 to 500 g/10 ares, and its application concentration is 0.01 to 30% when the emulsifable concentrate or wettable powder is used as aqueous dilute liquors.

These dosage rate and application concentration vary with the form of composition, application time, application scene, application method, kind of soil pest, degree of damage and the like, so that they may be increased or decreased independently of the foregoing ranges.

The controlling activity on soil pests of the present compound will be shown with reference to the following test examples. Every test example was carried out according to a three-replication test method. Of the test compounds, the present compounds are shown by Compound No. in Table 1, and compounds used as control are shown by Compound symbol in Table 2.

TABLE 2

| Compound symbol | Chemical formula | Remark |
|---|---|---|
| (A) | n-C$_3$H$_7$S\P(=O)/C$_2$H$_5$O  S—n-C$_3$H$_7$ | Ethoprophos |
| (B) | tert-C$_4$H$_9$S\P(=O)/C$_2$H$_5$O  S—sec-C$_4$H$_9$ | Compound described in International Patent Publication No. WO 83/00870 |
| (C) | n-C$_4$H$_9$S\P(=O)/C$_2$H$_5$O  S—n-C$_4$H$_9$ | Compound described in Japanese Patent Publication No. 29847/1969 |

TEST EXAMPLE 1

The emulsifiable concentrate of each test compound formulated according to Formulation example 1 was diluted with water, and 5 ml of the resulting aqueous dilute liquor was mixed with 50 g of soil (16 mesh) to make the concentration of active ingredient in soil 1 ppm. The soil was then placed in a polyethylene cup of 5.6 cm in diameter and 5.8 cm high, and two pieces of corn having roots of 2 to 3 cm long were planted. At the same time, ten third instar larvae of southern corn rootworm (Diabrotica undecimpunctata howardi Barber) were liberated in the cup. Two days after liberation, the number of the dead and alive of the larvae was examined to obtain mortality (%).

The result is shown in Table 3.

TABLE 3

| Test compound | Mortality (%) |
|---|---|
| (1) | 100 |
| (2) | 100 |
| (3) | 100 |
| (4) | 100 |
| (5) | 100 |
| (6) | 100 |
| (7) | 100 |
| (8) | 100 |
| (9) | 100 |
| No treatment | 0 |

TEST EXAMPLE 2

The emulsifiable concentrate of each test compound formulated according to Formulation example 1 was diluted with water, and 50 ml of the resulting aqueous dilute liquor was mixed with 500 g of soil (16 mesh) to make the concentrations of active ingredient in soil 0.5 and 0.25 ppm. The soil was then placed in a polyethylene cup of 12 cm in diameter and 8 cm high, and four pieces of corn having a bud of 5 to 6 cm long were planted. At the same time, twenty third instar larvae of southern corn rootworm (Diabrotica undecimpunctata howardi Barber) were liberated in the cup. Two days after liberation, the number of the dead and alive of the larvae was examined to obtain mortality (%).

The result is shown in Table 4.

TABLE 4

| Test compound | Mortality (%) 0.5 ppm | 0.25 ppm |
|---|---|---|
| (1) | 100 | 100 |
| (2) | 100 | 100 |
| (3) | 100 | 90 |
| (6) | 100 | 100 |
| (7) | 100 | 100 |
| (9) | 100 | 100 |
| (A) | 50 | 0 |
| (B) | 100 | 45 |
| (C) | 0 | 0 |

TEST EXAMPLE 3

A polyethylene cup of 12 cm in diameter 8 cm high was filled with soil infested with root-knot nematodes (Meloidogyne sp.), and three tomato seedlings at three- to four-leaf stage were planted. One day after planting, the emulsifiable concentrate of each test compound formulated according to Formulation example 1 was diluted with water to make the concentration of active ingredient 500 ppm, and the soil was drenched with 30 ml of the resulting aqueous dilute liquor. Eighteen days after drenching, the degree of insertion of the root-knot was observed with the naked eye and evaluated in six grades, 5, 4, 3, 2, 1 and 0, described below. The result is shown in Table 5.

| Evaluation value | Degree of insertion of root-knot |
|---|---|
| 5 | No insertion. |
| 4 | Insertion is less than 10% as compared with the untreated plot. |
| 3 | Insertion is 10 to 30% as compared with the untreated plot. |
| 2 | Insertion is 30 to 50% as compared with the untreated plot. |
| 1 | Much insertion similar to that in the untreated plot. |
| 0 | Same or more insertion as compared with that in the untreated plot. |

TABLE 5

| Test compound | Degree of insertion of root-knot |
|---|---|
| (2) | 4 |
| (5) | 5 |
| (6) | 4 |
| (A) | 3 |
| No treatment | 0 |

What is claimed is:
1. A dithiolphosphoric acid ester of the formula,

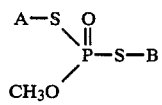

wherein A is sec-butyl or tert-butyl group, and B is iso-propyl, n-butyl, iso-butyl, sec-butyl or tert-butyl group.

2. The dithiolphosphoric acid ester according to claim 1, wherein both A and B are tert-butyl group.

3. A method for controlling soil pests which comprises applying a pesticidally effective amount of the dithiolphosphoric acid ester according to claim 1 to the soil pests.

4. A soil pesticidal composition which comprises an inert carrier and a pesticidally effective amount of dithiolphosphoric acid ester according to claim 1 as an active ingredient.

* * * * *